(12) United States Patent
Dibia

(10) Patent No.: US 11,195,118 B2
(45) Date of Patent: Dec. 7, 2021

(54) DETECTING HUMAN INPUT ACTIVITY IN A COGNITIVE ENVIRONMENT USING WEARABLE INERTIA AND AUDIO SENSORS

(71) Applicant: International Business Machines Corporation, Armonk, NY (US)

(72) Inventor: Victor C. Dibia, Whiteplains, NY (US)

(73) Assignee: International Business Machines Corporation, Armonk, NY (US)

( * ) Notice: Subject to any disclaimer, the term of this patent is extended or adjusted under 35 U.S.C. 154(b) by 1053 days.

(21) Appl. No.: 15/818,140

(22) Filed: Nov. 20, 2017

(65) Prior Publication Data

US 2019/0156219 A1 May 23, 2019

(51) Int. Cl.
| | |
|---|---|
| *G06N 20/00* | (2019.01) |
| *A61B 5/00* | (2006.01) |
| *A61B 5/11* | (2006.01) |
| *G06N 5/02* | (2006.01) |
| *G06F 1/16* | (2006.01) |
| *A61B 5/16* | (2006.01) |

(52) U.S. Cl.
CPC ............ *G06N 20/00* (2019.01); *A61B 5/1118* (2013.01); *A61B 5/681* (2013.01); *A61B 5/6824* (2013.01); *A61B 5/165* (2013.01); *G06F 1/163* (2013.01); *G06N 5/02* (2013.01)

(58) Field of Classification Search
CPC ........... G06N 5/02; G06N 20/00; G06F 1/163
See application file for complete search history.

(56) References Cited

U.S. PATENT DOCUMENTS

| 5,902,257 A | 5/1999 | Korth |
| 6,148,280 A * | 11/2000 | Kramer ............ A63B 69/3608 340/524 |
| RE40,993 E | 11/2009 | Westerman |
| 8,617,044 B2 | 12/2013 | Pelgrim et al. |
| 8,994,827 B2 | 3/2015 | Mistry et al. |

(Continued)

OTHER PUBLICATIONS

Xie, Hong-Bo et al.; Estimation of wrist angle from sonomyography using support vector machine and artificial neural network models; 2009 ELSEVIER; Medical Engineering & Physics 31 (2009) 384-391. (Year: 2009).*

(Continued)

*Primary Examiner* — Stanley K. Hill
(74) *Attorney, Agent, or Firm* — Stephen R. Tkacs; Diana R. Gerhardt; Stephen J. Walder, Jr.

(57) ABSTRACT

A mechanism is provided in a data processing system comprising a processor and a memory. The memory comprises instructions which are executed by the processor to cause the processor to be specifically configured to implement a recognizer module for detecting user input in a cognitive environment. The recognizer module receives sensor signals from at least one wearable device being worn by a user. The recognizer module analyzes the sensor signals using a machine learning model to determine at least one user input indicator describing user input activity of the user. The recognizer module communicates the at least one user input indicator to a cognitive system executing within the cognitive environment. The cognitive system performs at least one cognitive action based on the at least one user input indicator.

20 Claims, 4 Drawing Sheets

(56) References Cited

U.S. PATENT DOCUMENTS

| | | | |
|---|---|---|---|
| 9,044,172 B2* | 6/2015 | Baxi | A61B 5/1116 |
| 2011/0080290 A1* | 4/2011 | Baxi | A61B 5/1116 |
| | | | 340/573.1 |
| 2016/0196726 A1 | 7/2016 | Saito | |
| 2016/0253552 A1 | 9/2016 | Rihn et al. | |
| 2017/0011210 A1 | 1/2017 | Cheong et al. | |
| 2017/0020461 A1 | 1/2017 | Quinn et al. | |
| 2018/0132776 A1 | 5/2018 | Flickinger | |
| 2019/0150837 A1* | 5/2019 | Dibia | A61B 5/1118 |
| 2020/0371598 A1* | 11/2020 | Sadarangani | G06F 3/017 |

OTHER PUBLICATIONS

Henriksen, Andre et al.; Using Fitness Trackers and Smartwatches to Measure Physical Activity in Research: Analysis of Consumer Wrist-Worn Wearables; Journal of Medical Internet Research; pp. 1-19. (Year: 2018).*

Bunn, Jennifer A. et al.; Current State of Commercial Wearable Technology in Physical Activity Monitoring 2015-2017; Int J Exerc Sci 11(7): 503-515, 2018. (Year: 2018).*

List of IBM Patents or Patent Applications Treated as Related, Mar. 1, 2018, 2 pages.

Barreto, Armando et al., "Non-intrusive Physiological Monitoring for Automated Stress Detection in Human-Computer Interaction", Proceedings of International Workshop, HCI 2007 Rio de Janeiro, Brazil, Oct. 20, 2007 , 10 pages.

Hernandez, Javier et al., "Under Pressure: Sensing Stress of Computer Users", CHI 2104, Toronto, Ontario, Canada, Apr. 26-May 1, 2014, 10 pages.

Jimison, Holly et al., "Unobtrusive Monitoring of Computer Interactions to Detect Cognitive Status in Elders", IEEE Transactions on Information Technology in Biomedicine vol. 8, No. 3, Sep. 2004, 5 pages.

Serina, Elaine R. et al., "Wrist and forearm postures and motions during typing", http://www.tandfonline.com/doi/abs/10.1080/001401399185225, Ergonomics: vol. 42, No. 7, Published online Nov. 10, 2010, 6 pages. (Abstract Only).

Villani, Mary et al., "Keystroke Biometric Recognition Studies on Long-Text Input under Ideal and Application-Oriented Conditions", CVPRW'06, Conference on Computer Vision and Pattern Recognition Workshop, 2006, New York, NY, Jun. 17-22, 2006, 8 pages.

Vizer, Laura M., "Detecting Cognitive and Physical Stress Through Typing Behavior", CHI'09 Extended Abstracts on Human Factors in Computing Systems, Boston, MA, Apr. 4-9, 2009, 4 pages.

Wang, He et al., "Mole: Motion Leaks through Smartwatch Sensors", MobiCom '15, Paris, France, Sep. 15, 2015, 12 pages.

* cited by examiner

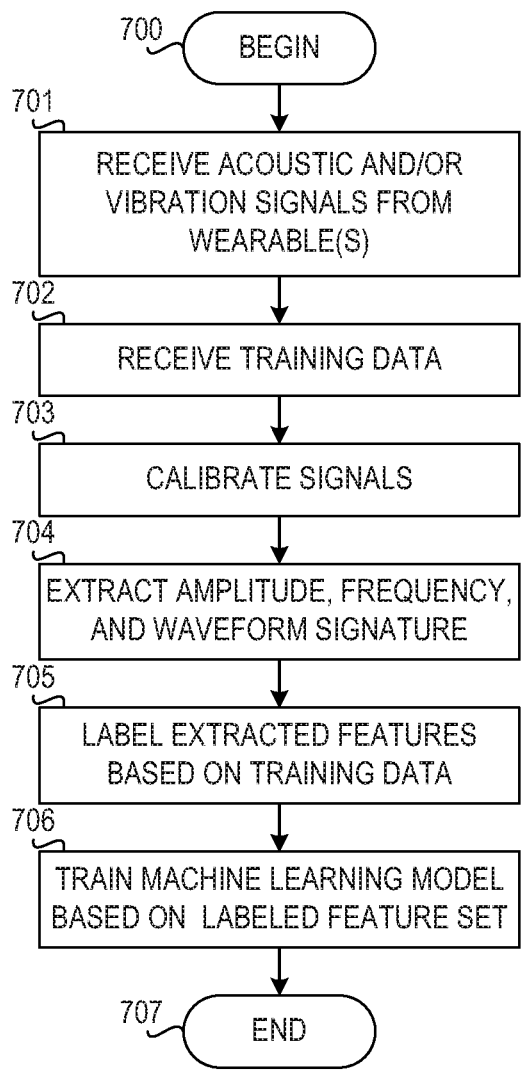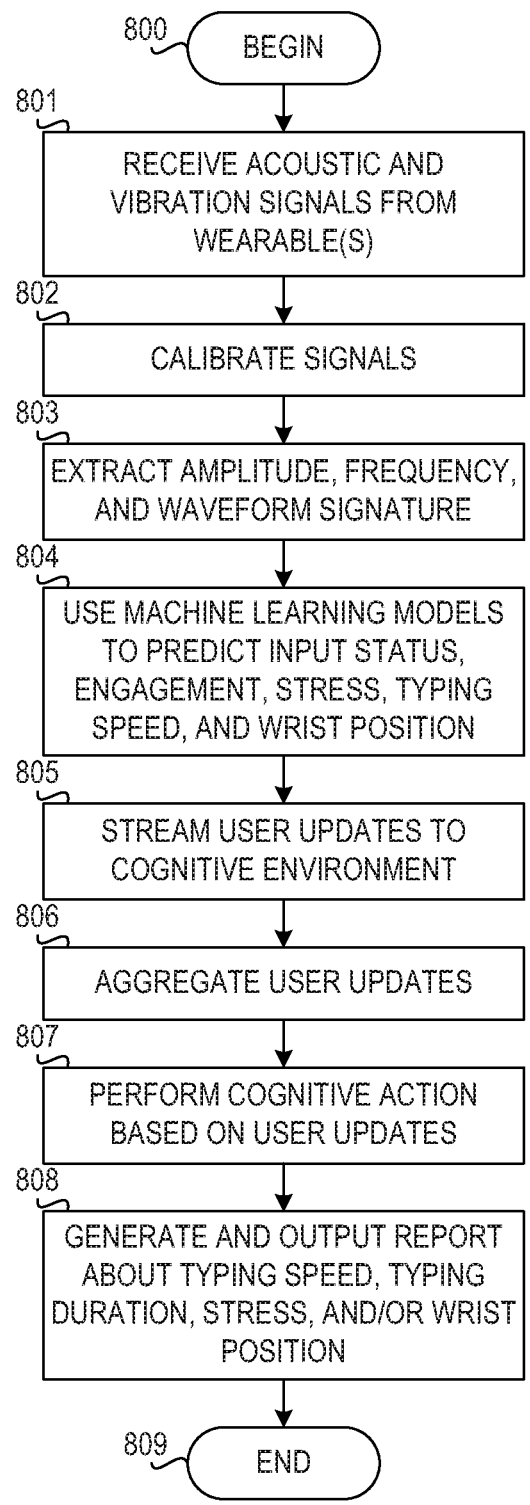

DETECTING HUMAN INPUT ACTIVITY IN A COGNITIVE ENVIRONMENT USING WEARABLE INERTIA AND AUDIO SENSORS

BACKGROUND

The present application relates generally to an improved data processing apparatus and method and more specifically to mechanisms for detecting human typing or handwriting activity in a cognitive environment using wearable inertia and audio sensors.

Wearable technology, wearables, fashionable technology, wearable devices, tech togs, or fashion electronics are smart electronic devices (electronic device with microcontrollers) that can be worn on the body as implants or accessories. Wearable devices, such as activity trackers, are a good example of the internet of things, since "things" such as electronics; software, sensors, and connectivity are effectors that enable objects to exchange data through the internet with a manufacturer, operator, or other connected devices, without requiring human intervention.

Wearable computers are miniature electronic devices that are worn under, with, or on top of clothing. This class of wearable technology has been developed for general or special purpose information technologies. It is also used in media development. Wearable computers are especially useful for applications that require more complex computational support, such as accelerometers or gyroscopes, than just hardware coded logic strained by the physical hardware of the system. One common feature of wearable computers is their persistence of activity.

An activity tracker, also known as a fitness tracker, is a device or application for monitoring and tracking fitness-related metrics such as distance walked or run, calorie consumption, and in some cases heartbeat and quality of sleep. The term is now primarily used for smartwatches that are synced, in many cases wirelessly, to a computer or smartphone for long-term data tracking.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method is provided in a data processing system comprising a processor and a memory wherein the memory comprises instructions which are executed by the processor to cause the processor to be specifically configured to implement a recognizer module for detecting user input in a cognitive environment. The method comprises receiving, by the recognizer module, sensor signals from at least one wearable device being worn by a user. The method further comprises analyzing, by the recognizer module, the sensor signals using a machine learning model to determine at least one user input indicator describing user input activity of the user. The method further comprises communicating, by the recognizer module, the at least one user input indicator to a cognitive system executing within the cognitive environment. The method further comprises performing, by the cognitive system, at least one cognitive action based on the at least one user input indicator.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE DRAWINGS

The invention, as well as a preferred mode of use and further objectives and advantages thereof, will best be understood by reference to the following detailed description of illustrative embodiments when read in conjunction with the accompanying drawings, wherein:

FIG. 7 is a flowchart illustrating operation of a mechanism for training a recognizer model for detecting human input activity for engagement assessment using wearable devices sensors in accordance with an illustrative embodiment; and FIG. 8 is a flowchart illustrating operation of a mechanism for detecting human input activity using wearable devices in accordance with an illustrative embodiment.

DETAILED DESCRIPTION

Figure 1:
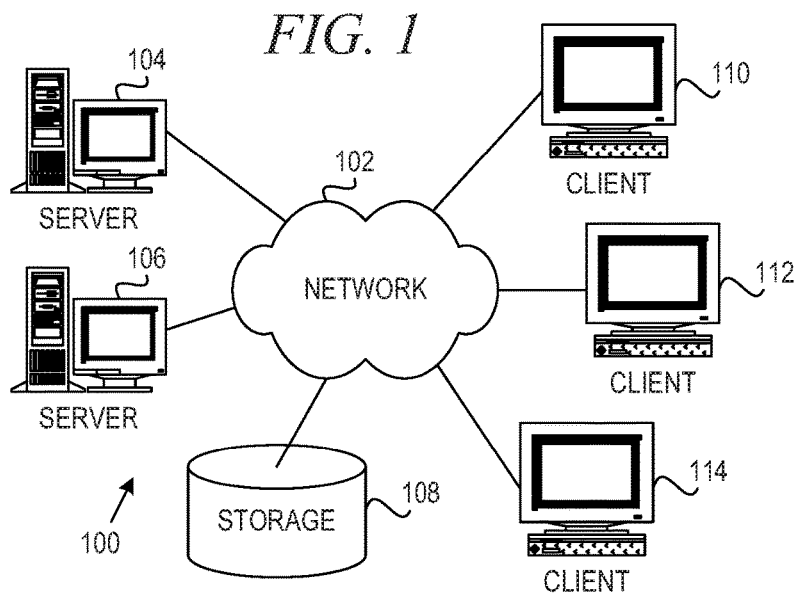
FIG. 1 is an example diagram of a distributed data processing system in which aspects of the illustrative embodiments may be implemented.

The illustrative embodiments provide a mechanism for accurate detection of multiple aspects of human typing or handwriting activity (typing activity recognition, typing speed recognition, wrist posture recognition, user stress patterns, etc.) based on an analysis of vibrations (accelerometer and gyroscope) from a wrist worn wearable device. The illustrative embodiments enable man and machine to work together to achieve goals beyond the reach of either man or machine. The illustrative embodiments are implemented as a system of components that provide capabilities to a cognitive environment. The illustrative embodiments provide mechanisms with capabilities pertinent to environments and scenarios that involve meeting and collaboration.

In the design of cognitive environments, tracking and responding to participant activity metrics such as typing and overall engagement remains an important challenge. Existing approaches in this domain rely on high resolution cameras, keyboard logging software, etc. Such approaches are limited by high costs associated with purchase, implementation, and limited of portable distribution across multiple environments, as well as camera occlusion issues.

The rapid commercialization of sophisticated wearables, such as smartwatches, as well as increased accuracy of their sensors, presents an opportunity for unobtrusively tracking participant activities within a cognitive environment. The illustrative embodiments use machine language (ML) analysis on inertia and audio sensor data. The illustrative embodiments are low cost, portable (publish and subscribe approach), and robust to occlusion as line-of-sight (LOS) is not required.

One example embodiment provides a mechanism for productivity assessment. The mechanism may augment document authoring tools using an untethered approach to unobtrusively track the amount of time a person spends typing or writing per day and to provide comprehensive writing metrics to writers (speed, typing posture, user stress, etc.). This can be integrated, e.g., as a plugin, into known document authoring and collaboration tools. Depending on the nature of the job, user input metrics may be an analog for work productivity. Thus, these plugins may be applied as a secondary tool to track productivity across multiple workstations without having to install any specialized software on these machines, such as keylogging software.

Another example embodiment provides a mechanism for typing education for "touch type" learning applications. Education applications that teach "touch typing" can leverage this mechanism to ascertain if a user is touch typing or "hunting and pecking," as well as an alternate approach to inferring typing speed. Users may be provided haptic feedback interventions to remind them to touch type. Initial tests show that vibration signals (amplitude and frequency) from a touch typing individual is distinct from one who is "hunting and pecking," and this can be used to predict the typing technique employed by the user.

Yet another embodiment provides a mechanism for typing posture tracking and carpal tunnel syndrome rehabilitation. Carpal tunnel syndrome is a debilitating as well as painful condition that impedes work productivity and is associated with the use of computing devices and typing activity. Research studies have shown a link between wrist angle (flexion and extension) and carpal tunnel pressure during typing. The mechanism of this embodiment provides an approach to design commercially viable intervention applications to help carpal tunnel syndrome in patients by monitoring their typing wrist angle, guiding them towards correct posture in order to reduce aggravated conditions.

A further embodiment provides a mechanism for integration with a cognitive environment. A wearable device with this mechanism, which is able to detect user input activity, typing speed, user stress, etc., may function as a cognitive object and relay valuable information regarding its wearer to the cognitive environment for processing. This information may improve the cognitive capabilities of the entire cognitive environment. For example, the cognitive environment may reduce the temperature or brighten the lights in response to stress or may decide not to interrupt the user if he is currently typing or writing.

Before beginning the discussion of the various aspects of the illustrative embodiments, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "component" or "engine," if used herein with regard to describing embodiments and features of the invention, is not intended to be limiting of any particular implementation for accomplishing and/or performing the actions, steps, processes, etc., attributable to and/or performed by the component. A component or engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular component or engine is, unless otherwise specified, for purposes of convenience of reference and not intended to be limiting to a specific implementation. Additionally, any functionality attributed to a component may be equally performed by multiple components, incorporated into and/or combined with the functionality of another component of the same or different type, or distributed across one or more components of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

Figure 2:
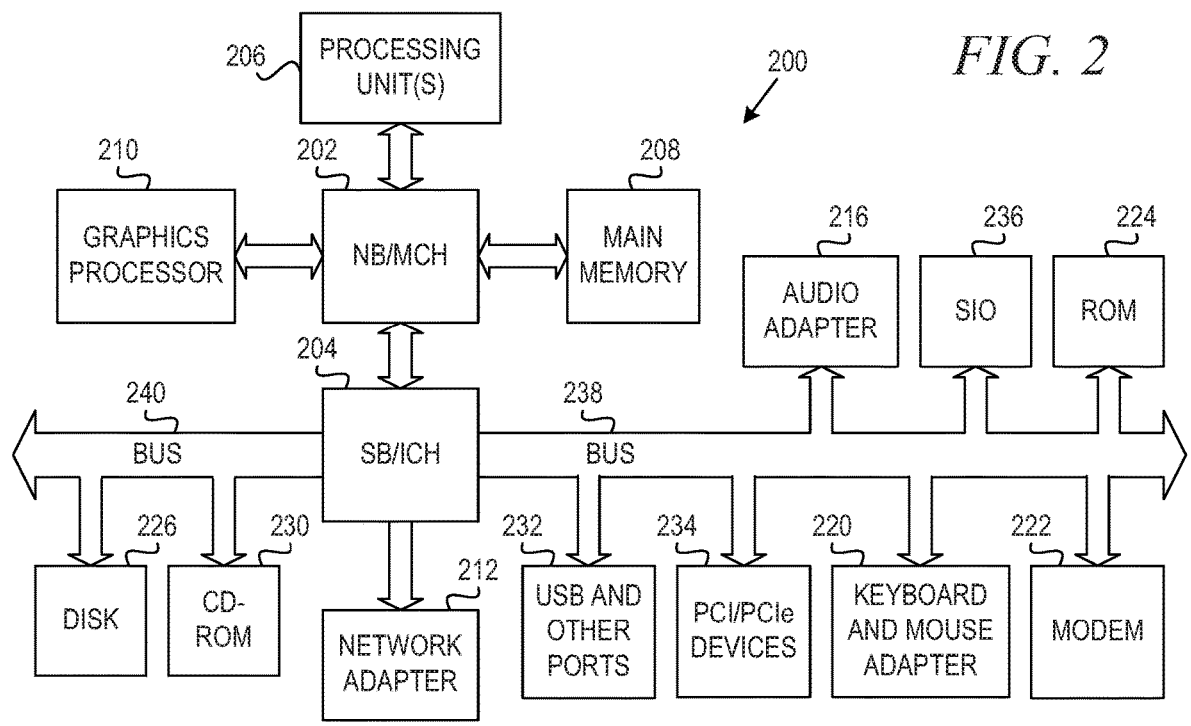
FIG. 2 is an example block diagram of a computing device in which aspects of the illustrative embodiments may be implemented.

The illustrative embodiments may be utilized in many different types of data processing environments. In order to provide a context for the description of the specific elements and functionality of the illustrative embodiments, FIGS. 1 and 2 are provided hereafter as example environments in which aspects of the illustrative embodiments may be implemented. It should be appreciated that FIGS. 1 and 2 are only examples and are not intended to assert or imply any limitation with regard to the environments in which aspects or embodiments of the present invention may be implemented. Many modifications to the depicted environments may be made without departing from the spirit and scope of the present invention.

FIG. 1 depicts a pictorial representation of an example distributed data processing system in which aspects of the illustrative embodiments may be implemented. Distributed data processing system 100 may include a network of computers in which aspects of the illustrative embodiments may be implemented. The distributed data processing system 100 contains at least one network 102, which is the medium used to provide communication links between various devices and computers connected together within distributed data processing system 100. The network 102 may include connections, such as wire, wireless communication links, or fiber optic cables.

In the depicted example, server 104 and server 106 are connected to network 102 along with storage unit 108. In addition, clients 110, 112, and 114 are also connected to network 102. These clients 110, 112, and 114 may be, for example, personal computers, network computers, or the like. In the depicted example, server 104 provides data, such as boot files, operating system images, and applications to the clients 110, 112, and 114. Clients 110, 112, and 114 are clients to server 104 in the depicted example. Distributed data processing system 100 may include additional servers, clients, and other devices not shown.

In the depicted example, distributed data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, the distributed data processing system 100 may also be implemented to include a number of different types of networks, such as for example, an intranet, a local area network (LAN), a wide area network (WAN), or the like. As stated above, FIG. 1 is intended as an example, not as an architectural limitation for different embodiments of the present invention, and therefore, the particular elements shown in FIG. 1 should not be considered limiting with regard to the environments in which the illustrative embodiments of the present invention may be implemented.

As shown in FIG. 1, one or more of the computing devices, e.g., server 104 may be specifically configured to implement a mechanism for detecting human input activity. The configuring of the computing device may comprise the providing of application specific hardware, firmware, or the like to facilitate the performance of the operations and generation of the outputs described herein with regard to the illustrative embodiments. The configuring of the computing device may also, or alternatively, comprise the providing of software applications stored in one or more storage devices and loaded into memory of a computing device, such as server 104, for causing one or more hardware processors of the computing device to execute the software applications that configure the processors to perform the operations and generate the outputs described herein with regard to the illustrative embodiments. Moreover, any combination of application specific hardware, firmware, software applications executed on hardware, or the like, may be used without departing from the spirit and scope of the illustrative embodiments.

It should be appreciated that once the computing device is configured in one of these ways, the computing device becomes a specialized computing device specifically configured to implement the mechanisms of the illustrative embodiments and is not a general purpose computing device. Moreover, as described hereafter, the implementation of the mechanisms of the illustrative embodiments improves the functionality of the computing device and provides a useful and concrete result that facilitates a mechanism for detecting human input activity.

As noted above, the mechanisms of the illustrative embodiments utilize specifically configured computing devices, or data processing systems, to perform the operations for detecting human input activity for engagement assessment using wearable inertia and audio sensors. These computing devices, or data processing systems, may comprise various hardware elements which are specifically configured, either through hardware configuration, software configuration, or a combination of hardware and software configuration, to implement one or more of the systems/subsystems described herein. FIG. 2 is a block diagram of just one example data processing system in which aspects of the illustrative embodiments may be implemented. Data processing system 200 is an example of a computer, such as server 104 in FIG. 1, in which computer usable code or instructions implementing the processes and aspects of the illustrative embodiments of the present invention may be located and/or executed so as to achieve the operation, output, and external effects of the illustrative embodiments as described herein.

In the depicted example, data processing system 200 employs a hub architecture including north bridge and memory controller hub (NB/MCH) 202 and south bridge and input/output (I/O) controller hub (SB/ICH) 204. Processing unit 206, main memory 208, and graphics processor 210 are connected to NB/MCH 202. Graphics processor 210 may be connected to NB/MCH 202 through an accelerated graphics port (AGP).

In the depicted example, local area network (LAN) adapter 212 connects to SB/ICH 204. Audio adapter 216, keyboard and mouse adapter 220, modem 222, read only memory (ROM) 224, hard disk drive (HDD) 226, CD-ROM drive 230, universal serial bus (USB) ports and other communication ports 232, and PCI/PCIe devices 234 connect to SB/ICH 204 through bus 238 and bus 240. PCI/PCIe devices may include, for example, Ethernet adapters, add-in cards, and PC cards for notebook computers. PCI uses a card bus controller, while PCIe does not. ROM 224 may be, for example, a flash basic input/output system (BIOS).

HDD 226 and CD-ROM drive 230 connect to SB/ICH 204 through bus 240. HDD 226 and CD-ROM drive 230 may use, for example, an integrated drive electronics (IDE)

or serial advanced technology attachment (SATA) interface. Super I/O (SIO) device 236 may be connected to SB/ICH 204.

An operating system runs on processing unit 206. The operating system coordinates and provides control of various components within the data processing system 200 in FIG. 2. As a client, the operating system may be a commercially available operating system such as Microsoft® Windows 7®. An object-oriented programming system, such as the Java™ programming system, may run in conjunction with the operating system and provides calls to the operating system from Java™ programs or applications executing on data processing system 200.

As a server, data processing system 200 may be, for example, an IBM eServer™ System p® computer system, Power™ processor based computer system, or the like, running the Advanced Interactive Executive (AIX®) operating system or the LINUX® operating system. Data processing system 200 may be a symmetric multiprocessor (SMP) system including a plurality of processors in processing unit 206. Alternatively, a single processor system may be employed.

Instructions for the operating system, the object-oriented programming system, and applications or programs are located on storage devices, such as HDD 226, and may be loaded into main memory 208 for execution by processing unit 206. The processes for illustrative embodiments of the present invention may be performed by processing unit 206 using computer usable program code, which may be located in a memory such as, for example, main memory 208, ROM 224, or in one or more peripheral devices 226 and 230, for example.

A bus system, such as bus 238 or bus 240 as shown in FIG. 2, may be comprised of one or more buses. Of course, the bus system may be implemented using any type of communication fabric or architecture that provides for a transfer of data between different components or devices attached to the fabric or architecture. A communication unit, such as modem 222 or network adapter 212 of FIG. 2, may include one or more devices used to transmit and receive data. A memory may be, for example, main memory 208, ROM 224, or a cache such as found in NB/MCH 202 in FIG. 2.

As mentioned above, in some illustrative embodiments the mechanisms of the illustrative embodiments may be implemented as application specific hardware, firmware, or the like, application software stored in a storage device, such as HDD 226 and loaded into memory, such as main memory 208, for executed by one or more hardware processors, such as processing unit 206, or the like. As such, the computing device shown in FIG. 2 becomes specifically configured to implement the mechanisms of the illustrative embodiments and specifically configured to perform the operations and generate the outputs described hereafter with regard to the mechanism for detecting human input activity.

Those of ordinary skill in the art will appreciate that the hardware in FIGS. 1 and 2 may vary depending on the implementation. Other internal hardware or peripheral devices, such as flash memory, equivalent non-volatile memory, or optical disk drives and the like, may be used in addition to or in place of the hardware depicted in FIGS. 1 and 2. Also, the processes of the illustrative embodiments may be applied to a multiprocessor data processing system, other than the SMP system mentioned previously, without departing from the spirit and scope of the present invention.

Moreover, the data processing system 200 may take the form of any of a number of different data processing systems including client computing devices, server computing devices, a tablet computer, laptop computer, telephone or other communication device, a personal digital assistant (PDA), or the like. In some illustrative examples, data processing system 200 may be a portable computing device that is configured with flash memory to provide non-volatile memory for storing operating system files and/or user-generated data, for example. Essentially, data processing system 200 may be any known or later developed data processing system without architectural limitation.

Figure 3:
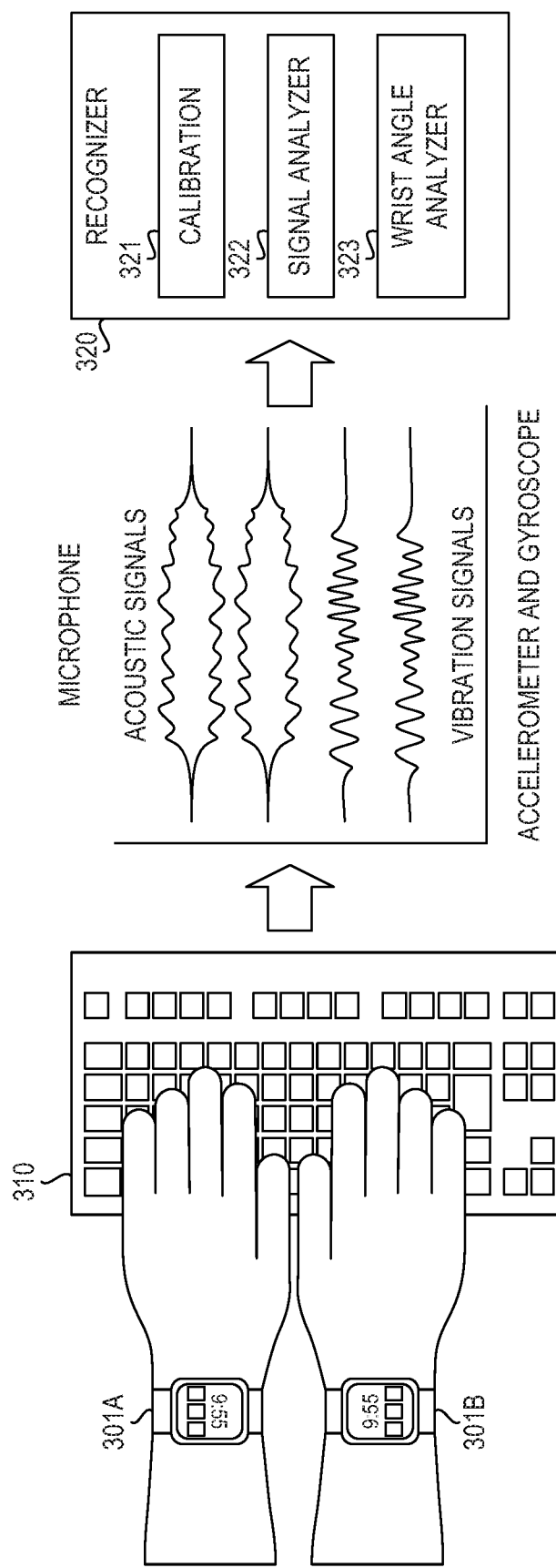
FIG. 3 illustrates core components of a mechanism for detecting human input activity using wearable inertia and audio sensors in accordance with an illustrative embodiment.

FIG. 3 illustrates core components of a mechanism for detecting human input activity using wearable inertia and audio sensors in accordance with an illustrative embodiment. A human user wears one or more wearable devices 301A, 301B while typing on keyboard 310. Wearable devices 301A, 301B may be any combination of existing wearable devices, such as smartwatches or fitness bands, or other types of wearable computer devices that may be worn on the fingers, hands, or wrists. Popular smartwatches and fitness bands include accelerometer and gyroscope devices, also referred to as inertia sensors, which generate signals representing movement of the wearable device. Smartwatches and fitness trackers currently use these sensors to measure steps or to detect when the wearer performs particular exercises. The accelerometer and gyroscope devices may also indicate the orientation of the wearable devices 301A, 301B during typing, from which the mechanism may predict the user's posture and wrist position.

One or both of wearable devices 301A, 301B may include a microphone that generates acoustic signals. For smartwatches in particular, it is common for wearable devices to include a microphone for conducting a telephone call, recording speech, or interacting with an intelligent assistant. In accordance with an illustrative embodiment, the acoustic signals may be analyzed to identify individual keyboard key presses. The acoustic signals may be analyzed in combination with vibration signals from the inertia sensors to detect human typing and predict typing speed. In one example embodiment, acoustic signals can be analyzed to differentiate between a mechanical keyboard and a touch keyboard.

In one example embodiment, wearables 301A, 301B may have other sensors that may be used for detecting human typing activity for engagement assessment. One or both of wearables 301A, 301B may have heart rate monitors. These signals may provide further data that can be modeled to predict human typing activity. Furthermore, heart rate signals may be analyzed to predict a user's stress level, which may be an analog for engagement or may indicate boredom or frustration.

As another example, global positioning system (GPS) sensors may be used to detect the user's location, which may be used to filter the other sensor data based on location. For example, if the GPS sensors indicate the user is viewing a presentation remotely at home, then detected typing may be given less weight when determining whether the user is engaged in the presentation. On the other hand, if the GPS sensors indicate the user is in her office, then detected typing may be given more weight when determining whether the user is being productive. The user's location may also provide an indication of the desk configuration to determine the user's anthropometry (table height, chair height, and hand position during typing). For example, the user may have a different desk configuration at the office than at home.

Recognizer 320 receives acoustic signals and vibration signals from wearable devices 301A, 301B. Calibration component 321 calibrates the sensor signals to the user's specific configuration. Recognizer 320 learns the user's typing vibration pattern and the x-y-z accelerometer position range as they type within the workspace. These values, in addition to acoustic signals, may be used as a composite vector to later detect typing activity. Calibration component 321 may use a machine learning model (not shown) to continuously learn as the user's signal data change over time.

Signal analyzer component 322 analyzes the acoustic signals and vibration signals to perform typing recognition. In accordance with the illustrative embodiments, signal analyzer component 322 performs typing activity recognition and typing speed recognition. Typing activity recognition involves fine grained and discriminant detection of typing activity based on training data from calibration component 321 (orientation and vibration patterns). Signal analyzer component 322 may also distinguish between touch typing and "hunt and peck" typing. Typing speed recognition involves analyzing frequency of vibrations to infer typing speed. Typing speeds are also used to calculate the number of words typed. Signal analyzer component 322 may use a machine learning model (not shown) to continuously learn as the user's signal data change over time.

In one embodiment, signal analyzer component 322 performs user stress recognition. Signal analyzer component 322 may analyze changes in typing vibrations (amplitude) to infer if the user is under some form of stress. The user may strike the keys harder during moments of stress, which will be reflected in the vibration signals and the acoustic signals. Signal analyzer component 322 leverages existing research that correlates user stress to pressure exerted on keys while typing.

In another embodiment, signal analyzer component 322 performs attention or engagement recognition. Signal analyzer component 322 monitors typing activity behavior over multiple meetings to estimate a user's engagement baseline over a time period. Some users may be habitual note-takers while others may not. This baseline may then be used to estimate attention/engagement during subsequent meetings.

In one embodiment, recognizer 320 may be used to detect user handwriting input, either using a pen or pencil on a pad of paper or on a tablet computer. Handwriting activity recognition involves fine grained and discriminant detection of handwriting activity based on training data from calibration component 321 (orientation and vibration patterns).

Figure 4:
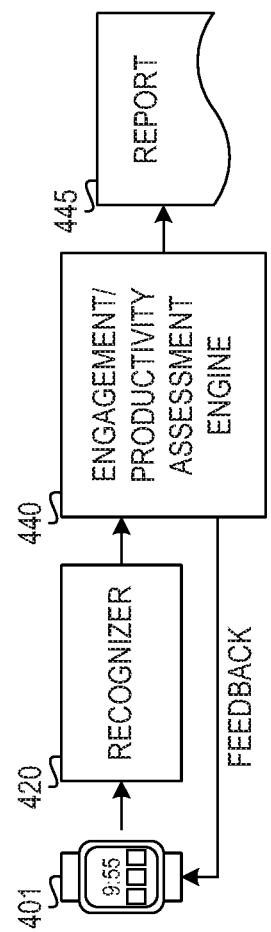
FIG. 4 is a block diagram illustrating a mechanism for engagement or productivity assessment in accordance with an illustrative embodiment.

FIG. 4 is a block diagram illustrating a mechanism for engagement or productivity assessment in accordance with an illustrative embodiment. Wearable device 401 sends acoustic signals from a microphone and/or vibration signals from accelerometer and gyroscope devices to recognizer 420. Wearable device 401 may be a smartwatch, fitness band, or similar device worn by the user on the hand or wrist. In one embodiment, the user may were such a device on one or both wrists. For example, the user may wear a smartwatch device on one wrist and a fitness band on the other wrist.

Recognizer 420 may be embodied within wearable device 401, within a smartphone device (not shown), a personal computer or table computer (not shown), or a server device. Wearable device 401 may communicate with a smartphone device or other computing device via wireless technology, such as Bluetooth™ wireless technology or cellular telephone data connection. Recognizer 420 generates indicator data for user input status, input duration, typing speed, wrist position, engagement, stress, etc. The user input status may indicate whether the user is typing or handwriting.

Engagement or productivity assessment engine 440 receives the indicator data and analyzes the data to generate a report 445 detailing the user's engagement or productivity. Engagement or productivity assessment engine 440 analyzes the data concerning user input status, input duration, typing speed, engagement, and stress and compares this data to times that the user is expected to be engaged in a meeting or is expected to be productivity. Report 445 provides statistics and suggestions about engagement or productivity.

In one embodiment, engagement or productivity assessment engine 440 generates and sends feedback to wearable device 401. The feedback may be in the form of a signal to activate a vibration device or notification in wearable device 401 in response to engagement or productivity assessment engine 440 determining that the user is not engaged or is not being productive. A notification may include text with information determined by engagement or productivity assessment engine 440. For example, the feedback may take the form of a notification stating: "You have not typed anything in the last ten minutes." A feedback may also include positive reinforcement. For instance, the feedback may take the form of a notification stating: "You have been typing for two hours straight. You have earned a break."

Returning to FIG. 3, wrist angle analyzer component 323 analyzes accelerometer and gyroscope signals to predict the user's posture and wrist position during typing activity. The accelerometer and gyroscope signals may be calibrated against a baseline example of proper posture and wrist position, and wrist angle analyzer component 323 may recognize changes in position that may lead to discomfort or health conditions, such as carpal tunnel syndrome.

Figure 5:
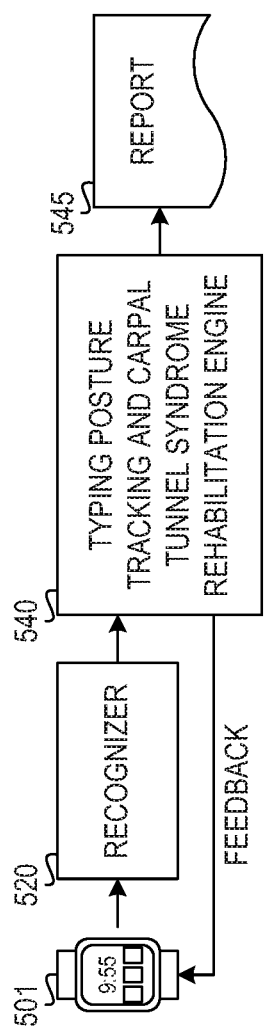
FIG. 5 is a block diagram illustrating a mechanism for typing posture tracking and carpal tunnel syndrome rehabilitation in accordance with an illustrative embodiment.

FIG. 5 is a block diagram illustrating a mechanism for typing posture tracking and carpal tunnel syndrome rehabilitation in accordance with an illustrative embodiment. Wearable device 501 sends acoustic signals from a microphone and/or vibration signals from accelerometer and gyroscope devices to recognizer 520. Wearable device 501 may be a smartwatch, fitness band, or similar device worn by the user on the hand or wrist. In one embodiment, the user may were such a device on one or both wrists. For example, the user may wear a smartwatch device on one wrist and a fitness band on the other wrist.

Recognizer 520 may be embodied within wearable device 501, within a smartphone device (not shown), a personal computer or table computer (not shown), or a server device. Wearable device 501 may communicate with a smartphone device or other computing device via wireless technology, such as Bluetooth™ wireless technology or cellular telephone data connection. Recognizer 520 generates indicator data for typing status, typing duration, typing speed, wrist position, engagement, stress, etc.

Typing posture tracking and carpal tunnel syndrome rehabilitation engine 540 receives the indicator data and analyzes the data to generate a report 545 detailing the user's typing posture, wrist position. Typing posture tracking and carpal tunnel rehabilitation engine 540 analyzes the data concerning tying status, typing duration, typing speed, engagement, and stress and compares this data to baseline signals for known good typing posture and wrist position. Report 545 may include details about the user's recent typing posture and wrist position, as well as hints for improving the typing posture or wrist position. Report 545 may include instructions to raise or lower the chair height relative to the keyboard, changing the angle of the keyboard, or the like. Report 545 may also include suggestions for new chairs, keyboard drawers, ergonomic keyboards, etc., to avoid problems based on the user's typing posture and wrist position.

In one embodiment, typing posture tracking and carpal tunnel syndrome rehabilitation engine 540 generates and sends feedback to wearable device 501. The feedback may be in the form of a signal to activate a vibration device or notification in wearable device 501 in response to typing posture tracking and carpal tunnel syndrome rehabilitation engine 540 determining that the user is using posture or wrist position that may contribute to carpal tunnel syndrome. A notification may include text with information determined by typing posture tracking and carpal tunnel syndrome rehabilitation engine 540. For example, the feedback may take the form of a notification stating: "Your wrists are too low relative to your keyboard." A feedback may also include more general instructions for preventing carpal tunnel syndrome. For instance, the feedback may take the form of a notification stating: "You have been typing for two hours straight. Please take a short break."

Figure 6:
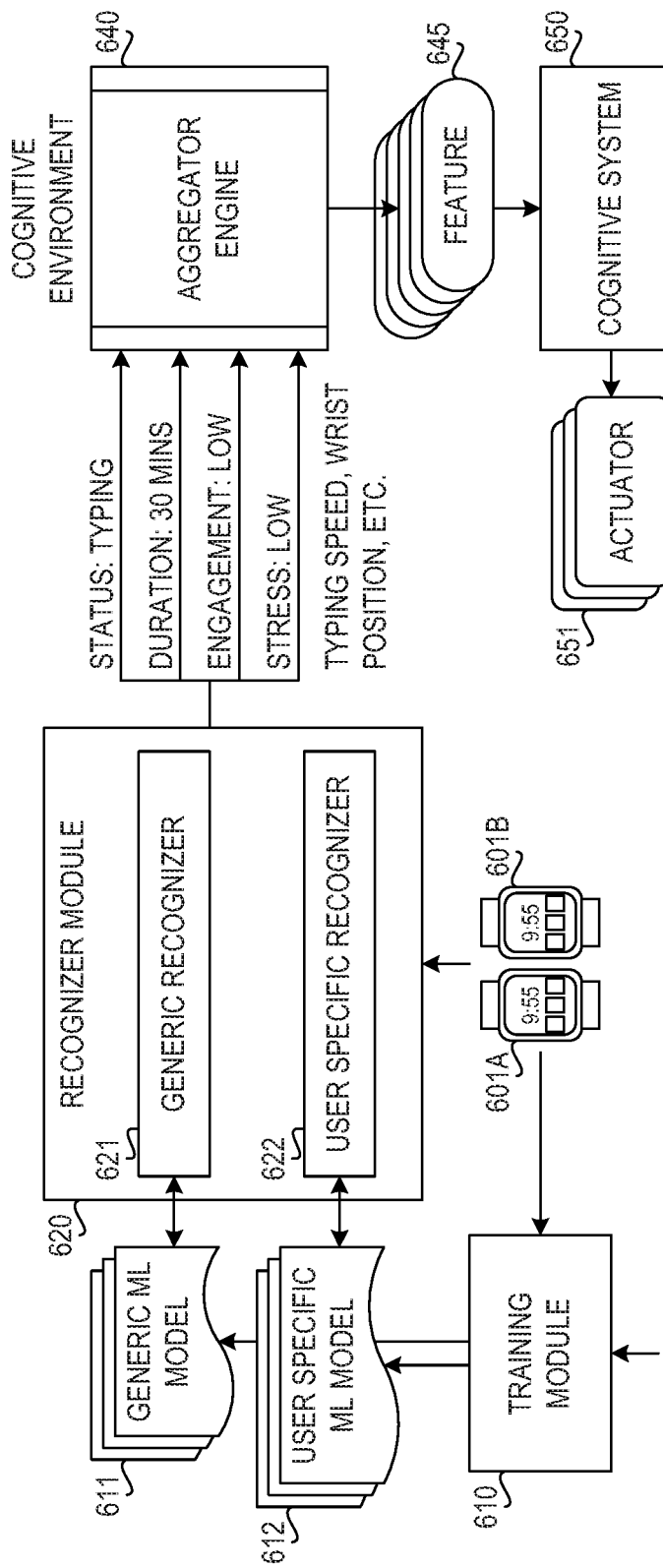
FIG. 6 is a block diagram of a mechanism for detecting human input activity in a cognitive environment in accordance with an illustrative embodiment.

FIG. 6 is a block diagram of a mechanism for detecting human input activity in a cognitive environment in accordance with an illustrative embodiment. Wearable devices 601A, 601B generate acoustic and/or vibration signals that result from a human wearer typing on a keyboard. As discussed above, wearable device 601A, 601B may be any combination of smartwatch devices, fitness bands, or similar wearable devices with microphones and/or accelerometer/gyroscope devices.

During training, training module 610 receives acoustic and/or vibration signals from wearable devices 601A, 601B. Training module 610 also receives training data to correctly classify the signals received from wearable devices 601A, 601B. The training data may include, for example, keylogging data, wrist position data, keyboard configuration, camera output, state feedback, etc. In another embodiment, the training data may include, for example, labeled handwriting input signals.

As one example, keylogging software may be installed on a computing device being used by the wearer of wearable devices 601A, 601B for training purposes only. At a minimum, keylogging software may determine which keys are being struck; however, keylogging software may also provide information about typing duration, typing speed, or the like. Alternatively, training module 610 may derive typing duration and typing speed from the individual key strike data.

As another example, wrist position data may be a measured value based on imaging processing of video received from a camera source. Alternatively, wrist position may be measured or estimated by an observer or self-reported by the wearer of wearable devices 601A, 601B. In one example embodiment, wrist position may be measured directly from accelerometer and gyroscope devices in wearable devices 601A, 601B.

As a further example, state feedback data may include observed or self-reported state information including engagement, productivity, stress level, etc. In one example embodiment, wearable devices 601A, 601B may generate heart rate signals, which may be correlated with reported stress levels. In another embodiment, accelerometer and gyroscope devices within wearable devices 601A, 601B may vary depending on the intensity of key strikes. As a user becomes more stressed, the user may apply more force on the keys, which may affect the amplitude of the acoustic and/or vibration signals.

As another example, keyboard configuration data may include information about the configuration of the user's chair, keyboard, desk, etc. For instance, an ideal chair configuration may be such that the user's upper legs are parallel to the floor with the feet flat on the floor, and an ideal keyboard configuration may be such that the user's wrists are at a predetermined downward angle while typing. The keyboard configuration data may also include a type of keyboard being used, e.g., mechanical, touch keyboard, laptop, ergonomic, etc. The keyboard configuration data may be entered by an observer, self-reported by the wearer of wearable devices 601A, 601B, or derived using image processing on video from a camera source.

In accordance with the illustrative embodiment, training module 610 uses training data to label the acoustic and/or vibration signals. Training module 610 uses the labeled data to generate generic machine learning (ML) models 611 for a large sample of different users with different training data. Training module 610 uses the labeled data of an individual user to generate user specific ML models 612. Recognizer module 620 includes a generic recognizer component 621 for generating typing indicators for generic users for which user specific ML models 612 have not been trained. Recognizer module 620 may also include user specific recognizer component 622 for generating typing indicators for a specific user for which user specific ML models 612 have been trained.

In one embodiment, generic ML models 611 and user specific ML models 612 include separate ML models for the various indicators being recognized. For instance, there may be separate ML models for typing status, typing speed, wrist position, engagement, stress, etc. A typing status ML model may be a classifier model that detects a binary typing/non-typing state. Typing speed, wrist position, stress level, and engagement ML models may be linear regression models that generate a numerical score value. Recognizer module 620 may use these models to generate any combination of the following typing indicators: status, typing duration, engagement, stress, typing speed, wrist position, productivity, etc.

During production runtime, recognizer module 620 receives acoustic and/or vibration signals from wearable devices 601A, 601B and applies one more of generic ML models 611 and user specific ML models 612 to the signals. Based on the application of the ML models, recognizer module 620 generates typing indicators, which may include one or more of the following: status, typing duration, engagement, stress, typing speed, wrist position, productivity, etc. These indicators may then be used for several applications, such as productivity/engagement assessment, education (touch type learning), health (typing posture and carpal tunnel syndrome rehabilitation), etc., as discussed above.

In accordance with an illustrative embodiment, aggregator engine 640 receives the user input indicator values from recognizer module 620 and streams user updates to a cognitive environment. A cognitive environment is an infrastructure inhabited by a society of "cogs" and the devices that let them behave as one shared integrated resource, enabling human-computer collaboration at the speed of thought. Cognitive environments can look and feel very different (from decision rooms in the workplace, to cars, to homes, to mobile), but by being connected to one another they feel seamless. As people inhabit and move across many physical environments, people experience a fluid, coherent computing experience through space and time, connected by an ecosystem of cognitive environments inhabited by a society of specialized software agents called "cogs." Cogs work in a mutually beneficial partnership with humans to enable better complex data-driven decision-making. Cogs are designed to follow and interact with humans and other cogs across a variety of everyday environments. They engage individually or collectively with humans through a combination of traditional interfaces and adaptive multimodal interfaces based upon spoken dialog, gesture, and advanced visualization and navigation techniques. They learn and leverage sophisticated models of human characteristics, preferences and biases so they can communicate naturally.

Thus, the mechanism for detecting human input activity of the illustrative embodiment may be embodied as a "cog" in a cognitive environment. A smartwatch device and/or smartphone device with the ability to detect user input activity, typing speed, user stress, etc. is able to function as a cognitive object or "cog" and relay valuable information regarding its wearer to the cognitive environment for processing. This information can improve the cognitive capabilities of the entire environment. Aggregator 640 generates features 645, which include features of the user, such as whether the user is currently typing or writing (i.e., engaged or productive), whether the user is stressed, the user's typing speed, the user's wrist position, etc. Cognitive system 650 receives and analyzes features 645 to interpret the user's state within the cognitive environment.

In one embodiment, cognitive system activates actuators 651 based on the features 645. For instance, if cognitive system 650 predicts that the user is stressed based on features 645, cognitive system 650 may activate actuators 651 to dim lights, close window blinds, or alter ambient lighting to calm the user. As another example, if cognitive system 650 predicts that the user is not being productive based on features 645, cognitive system 650 may activate actuators 651 to turn off the television or close the window blinds to eliminate distractions. Alternatively, if cognitive system 650 predicts that the user is being productive based on features 645, then cognitive system 650 may determine to not interrupt the user with an unimportant telephone call, email, question, or alert. In yet another example, if cognitive system 650 predicts that the user's wrist position may contribute to carpal tunnel syndrome based on features 645; cognitive system 650 may activate actuators 651 to adjust the user's chair or keyboard position.

In one embodiment, cognitive system 650 may be in a location other than the user's keyboard. For example, if the user leaves work after hours of intense typing and high stress levels, then when the user enters a car, cognitive system 650 may activate actuators 651 to play soothing music to relax the user. As the user moves from one environment to another, the features 645 of the use flow with him or her, and cognitive system 650 may use those features to improve the overall computing experience.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

FIG. 7 is a flowchart illustrating operation of a mechanism for training a recognizer model for detecting human input activity for engagement assessment using wearable devices sensors in accordance with an illustrative embodiment. Operation begins (block 700), and the mechanism receives acoustic and/or vibration signals from one or more wearable devices (block 701) and receives training data (block 702). The training data may include, for example, keylogging data, wrist position data, keyboard configuration, camera output, state feedback, etc.

The mechanism calibrates the signals to the user's anthropometry (block 703). Then, the mechanism extracts amplitude, frequency, and waveform signature features from the acoustic and/or vibration signals (block 704). The mechanism labels the extracted features based on the training data (block 705). The mechanism then trains one or more machine learning (ML) models based on the labeled feature set (block 706). The one or more ML models may include generic ML models and/or user specific ML models. There may be a different ML model for each user input indicator generated by the recognizer. Thereafter, operation ends (block 707).

FIG. 8 is a flowchart illustrating operation of a mechanism for detecting human input activity using wearable devices in accordance with an illustrative embodiment. Operation begins (block 800), and the mechanism receives acoustic and/or vibration signals from one or more wearable devices (block 801). The mechanism calibrates the signals (block 802) and extracts amplitude, frequency, and waveform signature features (block 803). The mechanism then uses machine learning models to predict user input status, engagement, stress, typing speed, and wrist position (block 804). The user input status may indicate whether the user is typing or performing handwriting input.

The mechanism streams user updates to a cognitive environment (block 805). An aggregator aggregates the user updates (block 806). A cognitive system in the cognitive environment performs a cognitive action based on the user updates (block 806). The cognitive action may include activating one or more actuators based on features of the user's status. For example, the cognitive action may comprise adjusting ambient lighting if the user is stressed or blocking distractions if the user is engaged or productive. As another example, the cognitive action may comprise adjusting the user's chair or keyboard position if the user's wrist position is likely to contribute to carpal tunnel syndrome.

The mechanism may also generate and output a report about typing speed; input duration, stress, and/or wrist position (block 808). In one embodiment, the mechanism a report may take the form of feedback provided to one or more of the wearable devices. The feedback may include a signal to activate a vibration device, a notification message to display to the user, an auditory alarm, or a voice message. Thereafter, operation ends (block 809).

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising a processor and a memory wherein the memory comprises instructions which are executed by the processor, the method comprising:
    receiving, by a recognizer module executing within the data processing system, sensor signals from at least one wearable device being worn by a user;
    analyzing, by the recognizer module, the sensor signals using a machine learning model to determine at least one user input indicator describing user input activity of the user, wherein the at least one user input indicator comprises a stress level indicator that indicates a stress level associated with the user input activity and wherein the recognizer module determines the stress level of the user based on an intensity of key strikes during the user input activity;
    communicating, by the recognizer module, the at least one user input indicator to a cognitive system executing within the data processing system; and
    activating, by the cognitive system, at least one actuator based on the at least one user input indicator.

2. The method of claim 1, wherein the sensor signals comprise at least one vibration signal from an accelerometer or gyroscope in the at least one wearable device.

3. The method of claim 2, wherein the at least one user input indicator comprises a wrist angle indicator that indicates an estimated wrist angle associated with the user input activity of the user.

4. The method of claim 3, wherein the at least one actuator comprises an actuator to adjust a chair height or an actuator to adjust a keyboard configuration.

5. The method of claim 1, wherein the sensor signals comprise at least one heart rate signal from a heart rate monitor in the at least one wearable device.

6. The method of claim 1, wherein the at least one actuator comprises at least one of an actuator to dim lighting, an ambient lighting actuator, an actuator to control music, or an actuator to control temperature.

7. The method of claim 1, wherein the machine learning model is a user-specific machine learning model trained for the user of the at least one wearable device.

8. The method of claim 1, wherein the at least one wearable device includes a smartwatch device.

9. The method of claim 1, wherein the at least one wearable device includes a fitness band.

10. A computer program product comprising a computer readable storage medium having a computer readable program stored therein, wherein the computer readable program, when executed on a processor of a data processing system, causes the data processing system to:
    receive, by a recognizer module executing within the data processing system, sensor signals from at least one wearable device being worn by a user;
    analyze, by the recognizer module, the sensor signals using a machine learning model to determine at least one user input indicator describing user input activity of the user, wherein the at least one user input indicator comprises a stress level indicator that indicates a stress level associated with the user input activity and wherein the recognizer module determines the stress level of the user based on an intensity of key strikes during the user input activity;
    communicate, by the recognizer module, the at least one user input indicator to a cognitive system executing within the data processing system; and
    activate, by the cognitive system, at least one actuator based on the at least one user input indicator.

11. The computer program product of claim 10, wherein the sensor signals comprise at least one vibration signal from an accelerometer or gyroscope in the at least one wearable device.

12. The computer program product of claim 11, wherein the at least one user input indicator comprises a wrist angle indicator that indicates an estimated wrist angle associated with the user input activity of the user.

13. The computer program product of claim 12, wherein the at least one actuator comprises an actuator to adjust a chair height or an actuator to adjust a keyboard configuration.

14. The computer program product of claim 10, wherein the at least one actuator comprises at least one of an actuator to dim lighting, an ambient lighting actuator, an actuator to control music, or an actuator to control temperature.

15. The computer program product of claim 10, wherein the at least one wearable device includes a smartwatch device or a fitness band.

16. The computer program product of claim 10, wherein the machine learning model is a user-specific machine learning model trained for the user of the at least one wearable device.

17. An apparatus comprising:
    a processor; and
    a memory coupled to the processor, wherein the memory comprises instructions which, when executed by the processor, cause the processor to:
    receive, by a recognizer module executing within the data processing system, sensor signals from at least one wearable device being worn by a user;
    analyze, by the recognizer module, the sensor signals using a machine learning model to determine at least one user input indicator describing user input activity of the user, wherein the at least one user input indicator comprises a stress level indicator that indicates a stress level associated with the user input activity and wherein the recognizer module determines the stress level of the user based on an intensity of key strikes during the user input activity;
    communicate, by the recognizer module, the at least one user input indicator to a cognitive system executing within the data processing system; and activate, by the cognitive system, at least one actuator based on the at least one user input indicator.

18. The apparatus of claim 17, wherein the sensor signals comprise at least one vibration signal from an accelerometer or gyroscope in the at least one wearable device, wherein the at least one user input indicator comprises a wrist angle indicator that indicates an estimated wrist angle associated with the user input activity of the user, wherein the at least one actuator comprises an actuator to adjust a chair height or an actuator to adjust a keyboard configuration.

19. The apparatus of claim 17, wherein the at least one actuator comprises at least one of an actuator to dim lighting, an ambient lighting actuator, an actuator to control music, or an actuator to control temperature.

20. The apparatus of claim 17, wherein the machine learning model is a user-specific machine learning model trained for the user of the at least one wearable device.

* * * * *